United States Patent
Martinez et al.

(10) Patent No.: US 7,619,724 B2
(45) Date of Patent: Nov. 17, 2009

(54) DEVICE AND METHOD FOR DETECTING CHANGES IN THE REFRACTIVE INDEX OF A DIELECTRIC MEDIUM

(75) Inventors: Borja Sepulveda Martinez, Madrid (ES); Gaspar Armelles Reig, Madrid (ES); Laura M. Lechuga Gomez, Madrid (ES); Ana Calle Martin, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 225 days.

(21) Appl. No.: 11/629,228

(22) PCT Filed: Jun. 10, 2005

(86) PCT No.: PCT/EP2005/006273
§ 371 (c)(1),
(2), (4) Date: Nov. 8, 2007

(87) PCT Pub. No.: WO2005/121754
PCT Pub. Date: Dec. 22, 2005

(65) Prior Publication Data
US 2009/0021727 A1    Jan. 22, 2009

(30) Foreign Application Priority Data
Jun. 11, 2004    (ES) .................... 200401437

(51) Int. Cl.
*G01N 21/41*    (2006.01)
*G01N 21/55*    (2006.01)

(52) U.S. Cl. ............... 356/128; 356/135; 356/136; 356/445

(58) Field of Classification Search ........... 356/128, 356/135, 136, 445
See application file for complete search history.

(56) References Cited

U.S. PATENT DOCUMENTS

| | | | | |
|---|---|---|---|---|
| 4,997,278 A | * | 3/1991 | Finlan et al. ........... | 356/128 |
| 5,327,225 A | * | 7/1994 | Bender et al. ......... | 356/445 |
| 5,374,563 A | * | 12/1994 | Maule .................. | 436/165 |

(Continued)

FOREIGN PATENT DOCUMENTS

WO    03/091713    11/2003

(Continued)

OTHER PUBLICATIONS

Hermann, C., et al. "Surface-enhanced magneto-optics in metallic multilayer films." *Physical Review B (Condensed Matter and Materials Physics)* APS through AIP USA (2001) vol. 64, No. 23, pp. 235422/1-11, 235422-4 and 235422-5.

*Primary Examiner*—Roy Punnoose
(74) *Attorney, Agent, or Firm*—Ladas and Parry LLP (57) ABSTRACT

The device for detecting changes in the refractive index of a dielectric medium comprises: at least one metallic layer (300) ready to be placed in contact with the dielectric medium (200); at least one light source (20) configured to direct transversal magnetic (TM) polarized light towards such metallic layer, so that the light is reflected on such metallic layer; coupling means (10); and at least one detector (31) configured to receive light reflected by the metallic layer and to detect at least one feature of such light. According to the invention, the metallic layer contains a ferromagnetic material. The invention also relates to a method.

45 Claims, 7 Drawing Sheets

U.S. PATENT DOCUMENTS

| | | |
|---|---|---|
| 5,485,277 A | 1/1996 | Foster |
| 5,815,278 A | 9/1998 | Johnston et al. |
| 5,912,456 A | 6/1999 | Melendez et al. |
| 5,991,488 A | 11/1999 | Salamon et al. |
| 2002/0009812 A1 | 1/2002 | Miura et al. |
| 2003/0103208 A1 | 6/2003 | Quinn et al. |

FOREIGN PATENT DOCUMENTS

| | | |
|---|---|---|
| WO | 03/104775 | 12/2003 |

\* cited by examiner

DEVICE AND METHOD FOR DETECTING CHANGES IN THE REFRACTIVE INDEX OF A DIELECTRIC MEDIUM

FIELD OF THE INVENTION

The invention lies within the field of detection of changes in refractive indexes of dielectric media, based on the surface plasmon resonance phenomenon.

BACKGROUND OF THE INVENTION

The detection of refractive index changes of dielectric media adjacent to a metallic surface by means of detection of the Surface Plasmon Resonance (SPR) is well known.

A surface plasmon wave is a magnetic transversal electromagnetic wave which propagates at the interface of a metal and a dielectric, where the metal behaves similarly to a free-electron gas. The plasma wave is characterized by a propagation vector (wave vector), which defines the conditions required for it to be excited. If the metallic and dielectric mediums are semi-infinite, the plasmon propagation vector $k_{SP}$ is given by the following equation:

$$k_{SP} = \frac{2\pi}{\lambda} \frac{n_m n_d}{\sqrt{n_m^2 + n_d^2}} = \frac{2\pi}{\lambda} \sqrt{\frac{\varepsilon_m \varepsilon_d}{\varepsilon_d + \varepsilon_d}}$$

where $\lambda$ is the wavelength, and $n_m$ and $n_d$ are, respectively, the refractive indexes of the metal and the dielectric (and $\in_m$ and $\in_d$ are their dielectric constants, with $n=\sqrt{\in}$).

Figure 1:
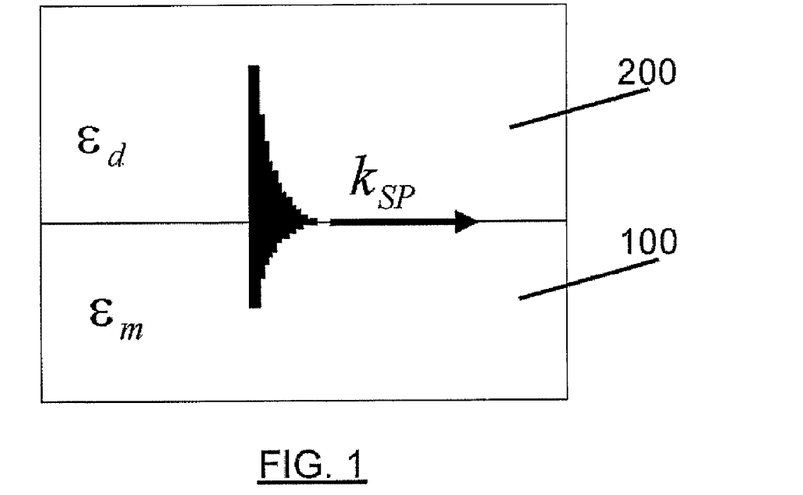
FIG. 1 briefly shows the arrangement of the electromagnetic field of a surface plasmon.

For the plasmon resonance phenomenon to be produced, the real part of the dielectric constant of the metal must be negative, $Re[\in_m]<0$, $Re[\in_d]<-Re[\in_m]$, and the wave produced must be transversal magnetic (TM). These conditions are fulfilled for several metals, amongst which the most widely used are gold and silver. The electromagnetic field of a surface plasma wave is characterized in that it has maximum intensity in the interface of the metal and the dielectric, and exponential decay in both media, as briefly shown in FIG. 1 (this figure shows the wave exponential decay in the interface of the metal 100 and the dielectric medium 200)

As a consequence, the excitation of the surface plasma wave will strongly depend on the dielectric constant (or refractive index) of the dielectric medium.

There are several ways of exciting these surface waves, e.g. by means of electrons or by means of light. However, the excitation of this surface plasmon wave cannot be produced by directly reflecting light on the metal. The reason for this being that the light wave vector follows the equation:

$$k_{LIGHT} = \frac{2\pi}{\lambda} \sqrt{\varepsilon_d} \sin\theta$$

where $\theta$ is the angle of light incidence and $\lambda$ is the wavelength. In order for the excitation to be produced, both wave vectors must be equal. Comparing the wave vectors of the plasmon and the wave vectors of the light, it follows that, for any angle of incidence of light:

$$|k_{LUZ}| < |k_{SP}|$$

Figure 2:
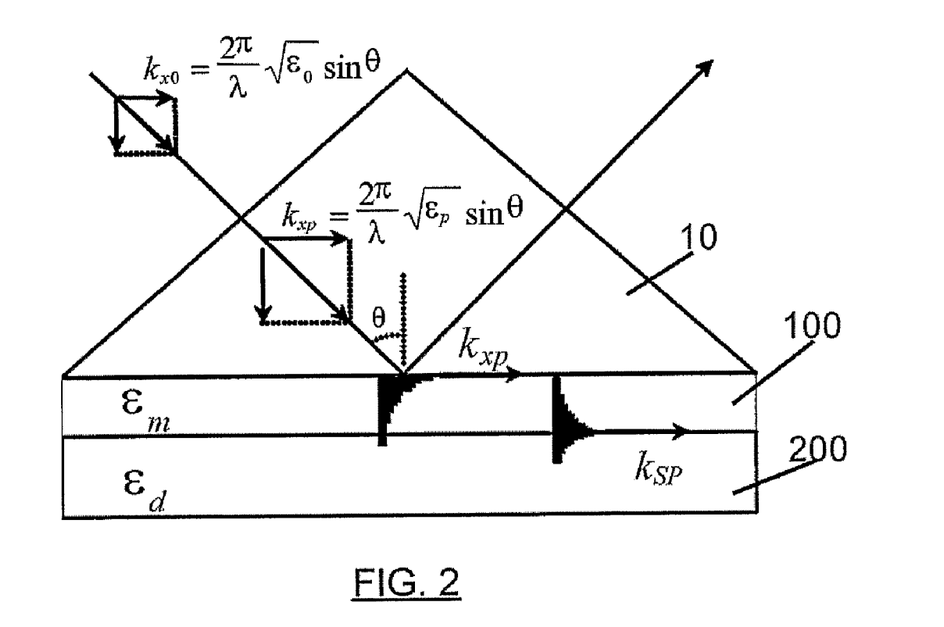
FIG. 2 briefly shows a conventional configuration for exciting the surface plasmon with light, based on prism coupling.

Several techniques are used to excite surface plasmon with light, amongst which we can highlight the following:

a) Prism coupling (diagrammatically shown in FIG. 2): a prism 10 is used, with a refractive index $n_p$ and a dielectric constant $\in_p$ larger that those of the dielectric medium 200 wherein the optic changes are to be produced ($\in_p > \in_d$), as well as a thin metal plate or layer with an specific thickness (depending on the light wavelength and on the metal used) placed between the prism 10 and the dielectric medium 200. In FIG. 2, $k_{x0}$ is the component of the light wave vector in the air, parallel to the reflection surface (and $\in_0$ is the dielectric constant of the air), $k_{xp}$ is the component of the light wave vector in the prism, parallel to the reflection surface (and $\in_p$ is the dielectric constant of the prism), and $k_{SP}$ is the propagation vector of the plasmon.

Excitation is produced by the complete internal reflection of the light on the interface between the prism and the metal, and plasmon is generated on the interface of the metal and the dielectric medium, whereon the measurement is to be made. In this configuration, the thickness of the metal layer is an essential parameter in order to observe the plasmon resonance. The optimal thickness can be estimated by several methods, e.g. through the formalism described in the article by M. Shubert, *Polarization-dependent optical parameters of arbitrarily anisotropic homogeneous layered media*, Physical Review B, vol. 53, p. 4265 (1996).

b) Designing a periodic structure, such as a grid, on the metal layer. In this way, a light diffraction phenomenon occurs, falling on the periodic structure and leading to an increase in the light wave vector:

$$k_{LIGHT} = \frac{2\pi}{\lambda} \sqrt{\varepsilon_d} \sin\theta + N \frac{2\pi}{\Lambda}$$

where $\Lambda$ is the period of the periodic structure and N is the order of light diffraction. The thickness of the metallic layer is not a very important parameter with this method, however, the period and depth of the periodic structure will be important.

c) By guiding light on a wave guide or on an optical fiber. Excitation is produced through the evanescent field of the light confined within the core of the guide or optical fiber.

These forms of exciting surface plasmon by light incidence are conventionally used (perhaps, particularly in the prism coupling-based system) in systems to measure/detect changes in the refractive indexes of dielectric media.

These measurement and detection systems are based on the fact that the excitation condition of the plasmon resonance depends on the refractive index, $n_d$ of the dielectric medium. This means that if the refractive index changes, the excitation condition of the plasmon will also change. This change in the resonance condition can be detected in different ways, e.g. by analysing the light reflected by the metal layer as a function of the angle of light incidence, by keeping the wavelength fixed, and in a configuration of prism coupling.

Figure 3A:
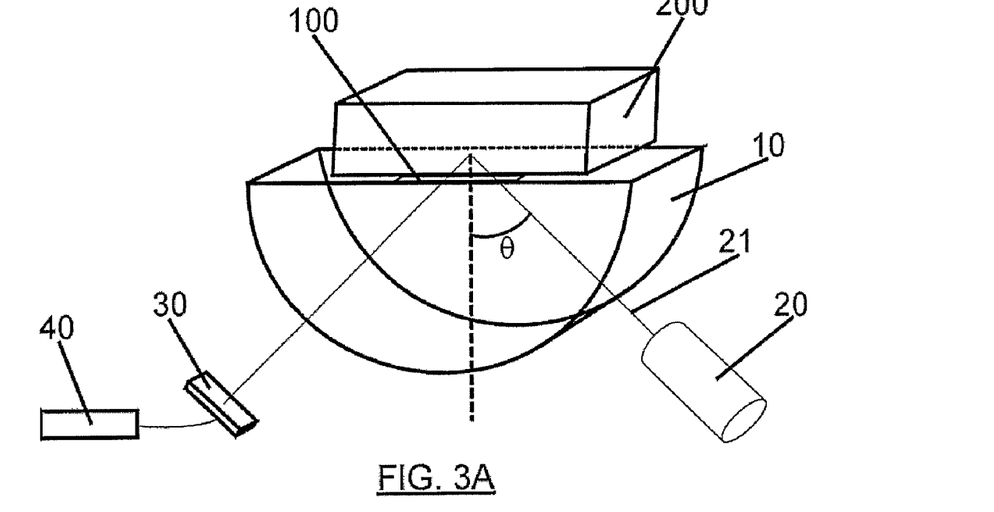
FIGS. 3A and 3B briefly show a system of change detection in the refractive index of a dielectric medium, according to the state of the art.

FIG. 3A shows a known configuration to detect changes in the refractive index of a dielectric medium, comprising a monochromatic light source 20 with transversal magnetic polarization (also known as "TM polarization" or "p polarization", i.e. with the electric field within the light incidence plane), a light intensity detector 30 connected to electronic data processing means 40 set up to analyse signals at the light intensity detector 30 output. In addition, the configuration comprises a coupling prism 10, a thin metallic layer 100 (normally gold) positioned on a prism surface 10, and, the dielectric media 200 (e.g. a fluid) on the other side of the metallic layer, i.e. in contact with the metallic layer surface, which is not in contact with the prism 10. The light 21 is reflected when falling on the metallic layer and the reflected light falls on the light detector 30, which detects its intensity, in turn recorded by the electronic data processing means 40.

Figure 3B:
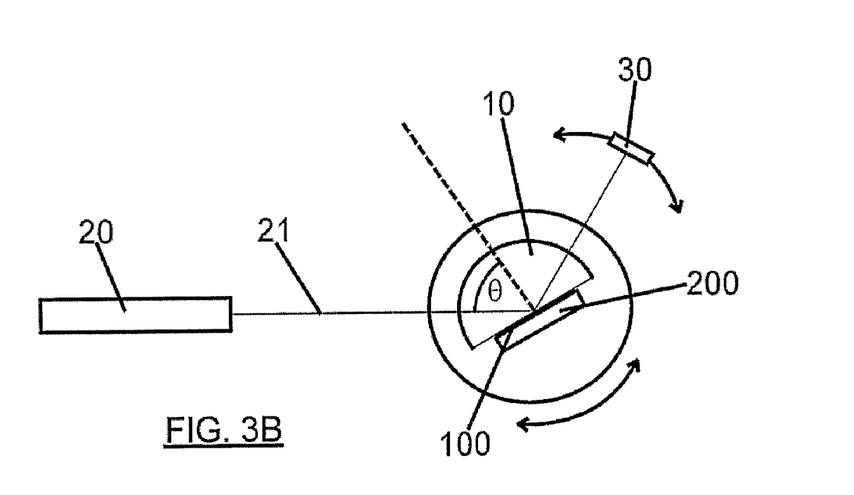

FIG. 3B diagrammatically shows how the prism 10 and the metallic layer 100 can be rotated in relation to the light source 20, so that the angle of light incidence θ 21 varies (this can be done by moving the light source and/or the unit formed by prism 10 and metallic layer 100).

As it gathered from the above explanation, the condition of plasmon excitation with light depends on several factors, such as the wavelength of the light, the angle of incidence θ, and the refractive index $n_d$. If the shown configuration starts from a small angle of incidence and this angle is increased, it reaches a point where the total reflection of the light on the prism 10 and the metal plate or layer 100 interface occurs. From this angle, if the angle of incidence θ continues to be increased, a strong decrease occurs in the reflected intensity, up to a minimum, which coincides with the excitation of the surface plasma wave on the other metal interface. Given that the excitation condition of the plasmon resonance depends on both the angle of incidence θ and the refractive index ($n_d$) of the dielectric medium, if the other variables are kept constant (e.g. the dielectric constant $\in_m$ and other features of the metallic layer, the light wavelength, etc.), a change in the refractive index ($n_d$) of the dielectric medium will correspond to a change in the angle of incidence θ, for which a minimum in the intensity of the reflected light occurs.

Figure 4:
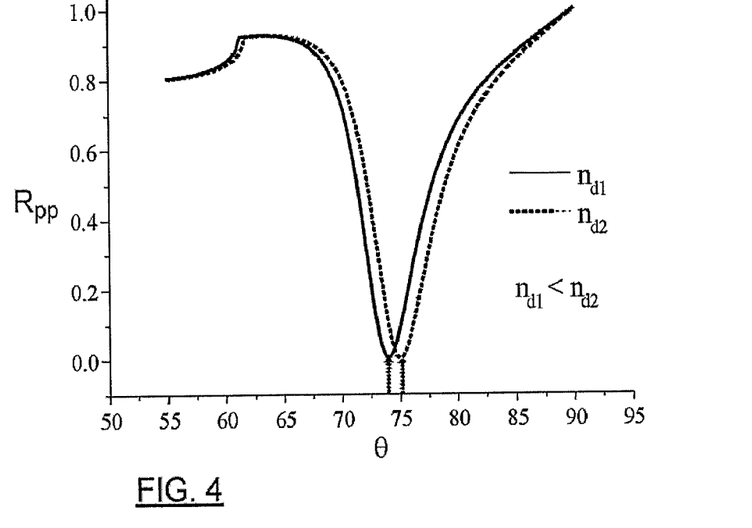
FIG. 4 is a diagram showing two curves which relate the intensity $R_{pp}$ of TM reflected light to different angles of light incidence θ, for two different refractive indexes ($n_{d1}$, $n_{d2}$) of the dielectric medium.

FIG. 4 shows two curves which relate the intensity $R_{pp}$ of the reflected light to the TM polarization (measured with the detector 30 of said configuration) as a function of the angle of incidence θ, for two different refractive indexes ($n_{d1}, n_{d2}$ with $n_{d1} < n_{d2}$). As can be observed, the increase in the refractive index from $n_{d1}$ to $n_{d2}$ is shown with a certain shift to the right in the $R_{pp}(\theta)$ curve diagram, due to the increase in the angle of incidence for which the plasmon excitation occurs. In this way, by making θ sweeps, the change in the angle for which the plasmon excitation occurs can be detected, and such change can be related to the variations in the refractive index of the dielectric medium 200.

That is to say, the quantification of the angle shift for which the resonance occurs, provides a measurement of the refractive index change. On the other hand, the sensitivity with which these changes of resonance angle can be detected, depends on how narrow the resonance curve is. The narrower the curve, the higher the sensitivity, and that will depend, in this case, on the metal used, on the layer thickness, and on the light wavelength. The configuration normally used is a 50 nm gold layer and light with a 632 nm wavelength.

An alternative way to detect changes in the refractive index can be to keep the angle of incidence θ constant, and to measure the changes in reflectivity (in the case of FIG. 4, if it is decided to keep the angle of incidence θ=72 degrees, an increase in the refractive index from $n_{d1}$ to $n_{d2}$ will be detected as a reflectivity increase, etc.). As in the previous case, the sensor's sensitivity depends on how narrow the resonance peak is.

If instead of varying the angle of incidence θ, we change the light wavelength, exactly the same occurs, the appearance of a resonance peak which moves when the refractive index of the dielectric medium adjacent to the gold layer is changed. This also applies to the case of excitation by means of a periodic structure or by means of a wave guide.

There are a great number of systems for detecting changes in refractive indexes based on surface plasmon resonance; examples of said systems are disclosed in:

U.S. Pat. No. 5,912,456
U.S. Pat. No. 5,485,277
U.S. Pat. No. 2003103208

Naturally, a direct application of this kind of sensor is the refractometer (for measuring refractive index changes). However, another important application of this kind of sensor at present is the biosensor or chemical sensor. The penetration distance of the evanescent field of the surface plasma wave within the dielectric medium is around 100 nm. Therefore, a biomolecular interaction occurring on the metallic layer surface will locally modify the surface refractive index. This variation will produce, in turn, a change in the propagation vector of the plasmon, and, as a consequence, in the resonance condition. This change can be detected by the abovementioned methods.

Figure 5:
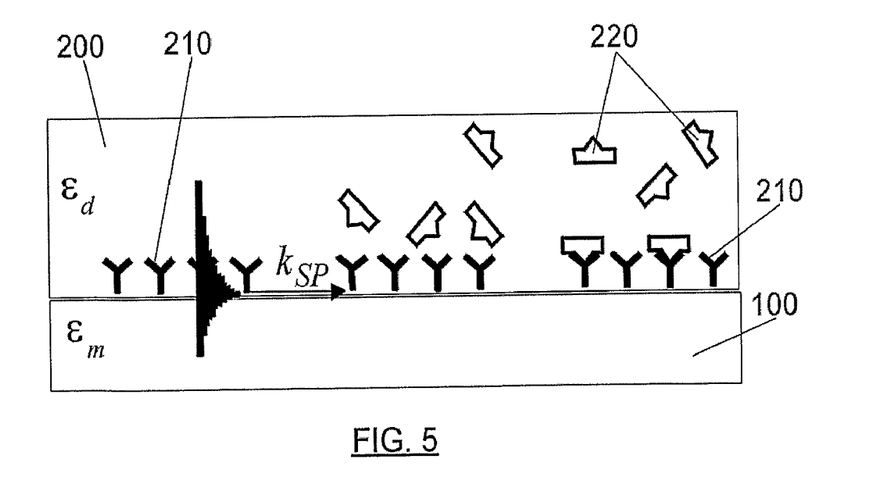
FIG. 5 briefly shows a detail of a surface plasmon resonance sensor in a biosensor application.

The use as biosensor can be based on the prior immobilization of receptor biomolecules 210 on the metallic layer surface 100, as diagrammatically shown in FIG. 5. These receptor biomolecules can be selectively bound to analyte molecules 220 which are to be detected and which can be present in a liquid that the metallic layer is in contact with. When the analyte molecules 220 are bound to the receptor molecules 210, a local change in the refractive index on the metallic surface will again occur which, in turn, will change the plasmon resonance condition.

Currently, there are multiple commercial devices and a great number of articles describing different types of measurement configuration and applications of this kind of sensors.

Surface plasmon resonance sensors generally are highly sensitive to detecting changes in refractive index, as well as low biomolecules concentrations. However, they may have sometimes insufficient sensitivity, e.g. currently, known sensors have problems in detecting changes in refractive index under $10^{-5}$ and molecules with a low molecular weight (lower than 1000 units of atomic mass), when used as biosensors. This means that detection of certain substances, such as chemical toxic substances or environmental polluting agents, is complex and cannot be performed directly and appropriately (using the abovementioned technology).

DESCRIPTION OF THE INVENTION

In order to solve these problems, an aim of the invention is to increase the sensitivity limit of the surface plasmon resonance sensors.

Figure 6:
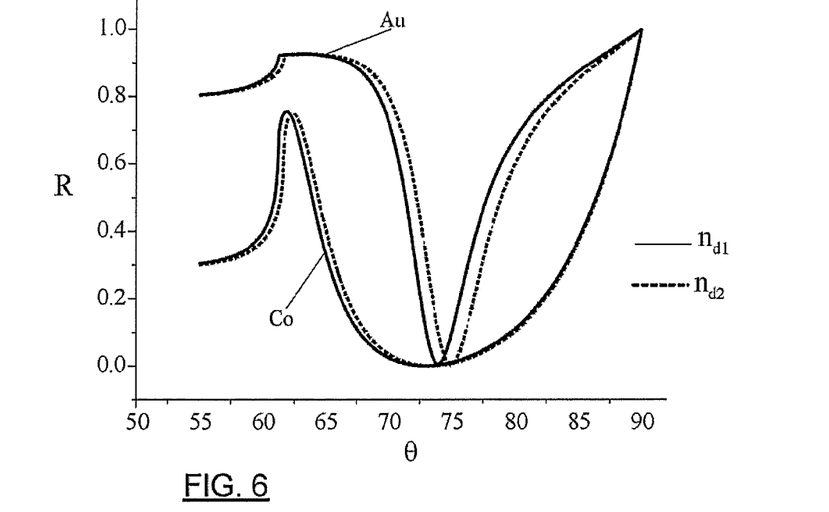
FIG. 6 is a diagram showing curves which illustrate the reflectivity $R_{pp}$ as a function of the angle of incidence θ for layers of different materials FIGS. 7A-7C briefly show different magnetization configurations of a layer of ferromagnetic material.

For this, the invention takes advantage of the fact that not only noble metals (such as gold, silver, etc.) allow the creation of surface plasma waves. There are also other metals, such as ferromagnetic metals (e.g. iron, cobalt or nickel), which have some optic properties that allow the creation of surface plasma waves. However, these plasmons show a high absorption, which is translated in very wide curves of plasmon resonance, as shown in FIG. 6, which compares the reflectivity of the TM polarized light ($R_{pp}$) according to the angle of incidence θ for a gold (Au) layer of 50 nm and another of cobalt (Co) of 20 nm (for two different refractive indexes $n_{d1}$ and $n_{d2}$ of the dielectric medium adjacent to the layers, $n_{d1} < n_{d2}$) and a wavelength of 632 nm. These wide curves imply, at first, low sensitivity in detecting changes in refractive indexes.

However, the ferromagnetic materials are magneto-optically active materials, i.e. they can change the optic properties of the light that interacts with them when they are subjected to a magnetic field that changes their magnetization state. Typical effects of these materials are rotation of the polarization plane of the light reflected and transmitted by the magnetic material, Kerr or Faraday rotation, respectively, as well as variations in the reflectivity and transmissibility, and dichroism or birefrigence effects.

Although, as stated above, the surface plasma wave in ferromagnetic materials has high absorption, the magneto-optic effects can be greatly increased when the plasmon is excited on these layers, as shown in the following articles:

P. E. Ferguson, O. M. Stapsudd, and R. F. Wallis, *Enhancement of the transverse Kerr magneto-optic effect by surface magnetoplasma waves*, Physica vol. 89B, pp. 91-94 (1977)

C. Hermann, V. A. Kosobukin, G. Lampel, et al, *Surface-enhanced magneto-optics in metallic multilayer films*, Phys. Rev. B, vol. 64, 235422 (2001)

Figure 7A:
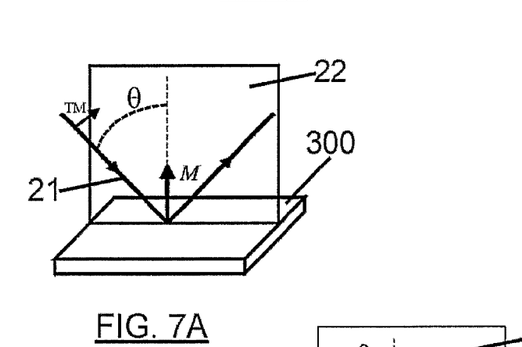
Figures 7B, 7C:
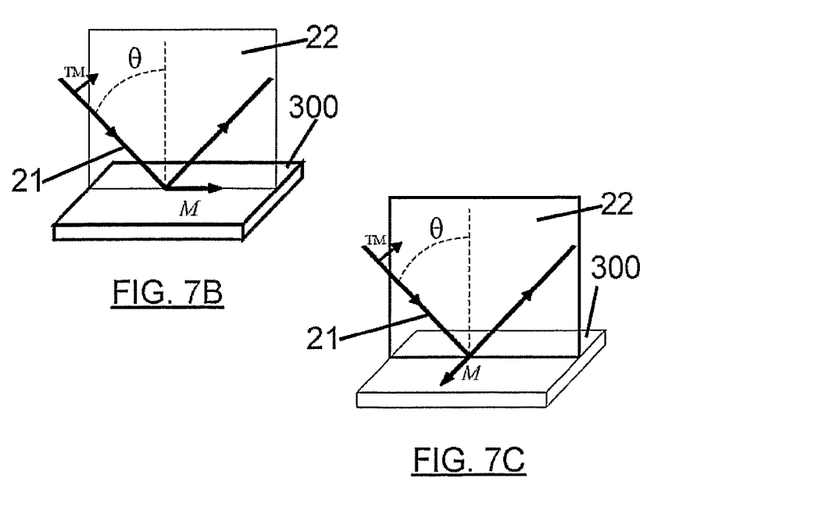

The magneto-optic effects depend on the orientation of the magnetization; FIGS. 7A-7C briefly show the magnetization of a layer 300 of a ferromagnetic material whereon a TM polarized light ray 21 falls (i.e. with the electric field inside the light incidence plane 22), namely:

FIG. 7A: polar configuration, i.e. the magnetization M is perpendicular to the layer plane.

FIG. 7B: longitudinal configuration, i.e. with magnetization M parallel to plane 22 of light incidence and parallel to the layer plane.

FIG. 7C: transversal configuration, i.e. with magnetization M perpendicular to plane 22 of light incidence and parallel to the layer plane.

Figure 8:
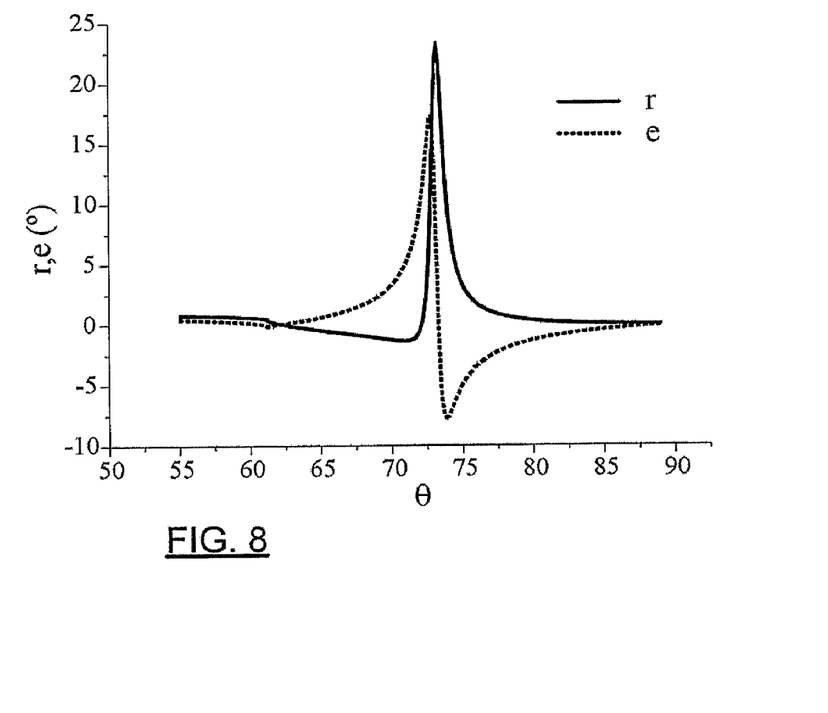
FIG. 8 is a diagram showing the rotation and ellipticity as a function of the angle of light incidence θ on a layer of ferromagnetic material with magnetization in polar configuration.

Therefore, such magneto-optic effects when plasmon is excited could be divided in:

a) Increase in the rotation and ellipticity of the polarization plane of the reflected light, when the magnetization is in polar configuration. FIG. 8 shows examples of "r" rotation and "e" ellipticity as a function of the angle of incidence θ of the light 21, in prism coupling configuration, on a layer of ferromagnetic material, in this case, on a 20 nm cobalt layer, with polar magnetization.

b) Increase in the rotation and ellipticity of the polarization plane of the reflected light, when the magnetization is in longitudinal configuration. In this configuration, the magneto-optic effects are, generally, lower than in polar configuration.

c) Increase in relative variations $\delta_{pp}$ of reflectivity $R_{pp}$ for TM polarized light, when magnetization is in transversal configuration, and that could be defined as the difference in the reflectivity ($R_{pp}$) between 2 given transversal states of magnetization ($M_1$ and $M_2$), divided by the reflectivity in a reference magnetization state ($M_{ref}$):

$$\delta_{pp} = \frac{\Delta R_{pp}}{R_{ppREF}} = \frac{R_{pp}(M_1) - R_{pp}(M_2)}{R_{pp}(M_{ref})}$$

The 2 given states of magnetization can be those corresponding to saturation magnetization M in opposite directions, i.e.:

$$\Delta R_{pp} = R_{pp}(M) - R_{pp}(-M)$$

but, it is also possible to measure the reflectivity in non-opposite magnetization states, for example:

$$\Delta R_{pp} = R_{pp}(M) - R_{pp}(0)$$

Regarding the reflectivity of reference, it is normally considered:

$$R_{pp}(M_{ref}) = R_{pp}(0)$$

although the following, amongst others, could be used:

$$R_{pp}(M_{ref}) = \frac{R_{pp}(M) + R_{pp}(-M)}{2}$$

Figure 9:
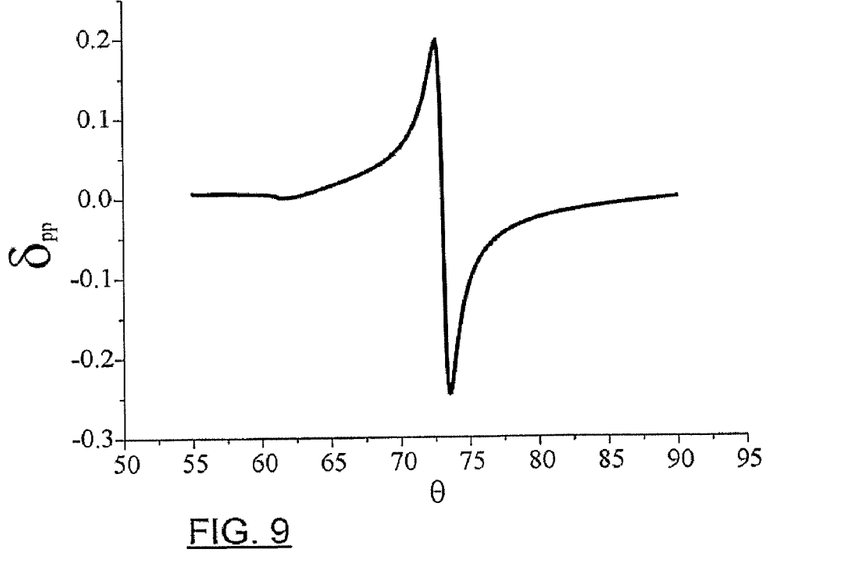
FIG. 9 is a diagram showing the relative variations of the reflectivity $\delta_{pp}$ as a function of the angle of light incidence, with magnetization in transversal configuration.

FIG. 9 shows the relative variation of the reflectivity $$\delta_{pp} = \frac{R_{pp}(M) - R_{pp}(0)}{R_{pp}(0)}$$

as a function of the angle of incidence of light θ, in prism coupling configuration, for a 20 nm cobalt layer, in transversal magnetization configuration. Therefore, in this measurement configuration, a sequential variation of the transversal magnetization state between states $M_1$ and $M_2$ is required, which can be obtained, for example, by inducing a rotating magnetization on the layer.

Such increases on the magneto-optic effects in the presence of surface plasmon waves have been used in magneto-optic transducers for reproducing information recorded in a magnetic medium, as disclosed in, for example, U.S. Pat. No. 3,636,535 and U.S. Pat. No. 3,545,840.

The invention is based on the innovative idea of taking advantage of the magneto-optic effects in the presence of surface plasma waves in order to improve the sensitivity of the refractive index sensors based on surface plasmon resonance. That is to say, the invention is based on the combination of the magneto-optic effects of ferromagnetic metals and the surface plasmon resonance on the interface of a metal and a dielectric. The conjunction of these two phenomena produces an increase in the magneto-optic effects. Such increase in the magneto-optic effects, as in the case of conventional plasmon resonance, depends on the refractive index of the dielectric medium in contact with the surface plasmon. The increase in the magneto-optic effects will be very localized in the plasmon resonance. Therefore, it will be extremely sensitive to the changes in refractive index, and will allow the increase in the sensor sensitivity limit. Therefore, small changes in the refractive index will produce great variations in the measured magneto-optic effects.

In this way, a first aspect of the invention relates to a device for detecting changes in the refractive index of a dielectric medium. The device comprises, at least, the following components:

At least one metallic layer configured to be placed in contact with the dielectric medium (e.g. in direct contact with the dielectric medium, or separated from the dielectric medium by one or several additional layers, which can have a protective effect).

At least one light source configured to direct transversal magnetic polarized light (also known as "TM polarization" or "p polarization", i.e. with the electric field inside the plane of light incidence) towards such metallic layer, so that the light reflects on such metallic layer.

Coupling means associated to such light source and to such metallic layer, so that the light can excite the surface plasmon resonance on the metallic layer when falling on the metallic layer. Such coupling means can be comprised of a prism with a refractive index greater than the dielectric medium on which the measurement is to be performed (the metallic layer can be deposited on one of the prism surfaces, so that the light reaches the layer through the prism). Alternately, coupling means can consist of a periodic structure, such as a grid, on the surface of the metallic layer upon which the light falls, or of a wave guide or optical fiber which receives the light so that such light propagates through the guide, and that its evanescent field can excite the plasmon on the metallic layer(s). There is a great number of coupling means conventionally used in this type of devices and such means can be applied directly to the invention, in a conventional way.

At least one detector configured to receive light reflected by the metallic layer and to detect, at least, one feature of such reflected light (e.g. its rotation, ellipticity and/or intensity); the detector can produce an output signal related to (e.g. proportional to) a value of the detected feature.

According to the invention, the metallic layer (or, if there are several metallic layers, at least one of them) has a ferromagnetic material (e.g. iron, cobalt or nickel). For example, the metallic layer can:

be made of ferromagnetic material (only one ferromagnetic material or a combination of several ferromagnetic materials);

be an alloy of at least one ferromagnetic material and at least one non-ferromagnetic material;

be formed by magnetic particles (e.g. nanoparticles, microparticles, etc.) embedded in a metallic medium (e.g. cobalt particles in gold); or be formed by a set of metallic particles that have ferromagnetic material embedded in a dielectric medium.

Despite the fact that a ferromagnetic material could seem, at first sight, less suitable for this type of application than the metals conventionally used (mainly, gold and silver, which show much narrower plasmon resonance curves in reflectivity than those shown by ferromagnetic materials), their use enables sensitivity to be increased, if we take advantage of the increase of magneto-optic effects by means of plasmon resonance. In this way, the sensor or detector, according to the invention, and with the layer with ferromagnetic material conveniently magnetized, permits producing a great increase in the sensitivity.

The device can comprise magnetization means configured to magnetize the metallic layer. These magnetization means can be controlled by a general control system of the device and be formed by a magnet, an electromagnet, coils, etc.

The magnetization means can be configured to magnetize the metallic layer in polar, longitudinal, and/or transversal configuration, or any combination thereof, for example, according to the instructions of the control system. The choice of the magnetization orientation will depend on the light features one wishes to detect and taken as a base to later determine the changes in the refractive index of the dielectric medium. For example, the magnetization in polar or longitudinal configuration may be suitable if the light feature one wishes to measure is its rotation (r) and/or ellipticity (e). On the other hand, magnetization in transversal configuration may be preferable if the choice is to measure the intensity of the reflected light $R_{pp}$, and to base the analysis on the relative differences $\delta_{pp}$ in such intensity, depending on how the magnetization state between two given states is varied.

In the case of magnetization in polar or longitudinal configuration, if the incidence is made with TM polarized light, the reflected beam will have TE (transversal electric) and TM components, due to light rotation. The rotation and ellipticity are defined from the angle and the phase shift between the TM component and the vector resulting from the vectorial sum of the reflected TE and TM components. Logically, the intensities in each polarization (Rpp and Rps) could be measured using an optic component separating the 2 polarizations and 2 light detectors: the optic component separates both polarizations, which are simultaneously measured by different detectors. For example, it can be measured by seeking the angle of the optic component which makes the difference between both signals 0, by detecting the appropriate combination of TE and TM components, etc.

The magnetization means can be configured to be able to change the state (i.e. direction and/or module/magnitude) of the metallic layer magnetization sequentially, which is required in the case of magnetization in transversal configuration and which can be achieved, for example, by rotating the magnetization on the plane of the metallic layer, which can be very simply implemented by means of electromagnets, coils or simple magnets arranged in a rotating way. In this way, the relative variations of light reflectivity, $\delta_{pp}$, can be measured (using the detector, and in a synchronized way with the magnetization rotation) when the magnetization rotates inside the plane of the metallic layer, as a base for determining the changes in the refractive indexes.

The change in magnetization state can be useful not only in the case of transversal magnetization, but also in configurations of polar or longitudinal magnetization, since being able to vary the magnetization in a sequential way periodically, allows a synchronous or in-phase detection, or a Fourier analysis, to be performed. Therefore, if the magnetization state M varies periodically, the reflectivity also varies periodically ($R_{pp}$(M cos wt)).

The reflectivity can be broken down in a Fourier series:

$$R_{pp}(M \cos wt) = R_{pp}(0) + R_{pp}(1w) + R_{pp}(2w) + \ldots$$

as a function of the different harmonics. So that a Fourier analysis of the first harmonic will give the term $R_{pp}(1w)$ So:

$$\delta_{pp} = \frac{\Delta R_{pp}}{R_{ppREF}} = \frac{R_{pp}(M) - R_{pp}(0)}{R_{pp}(0)} \approx \frac{R_{pp}(1w)}{R_{pp}(0)}$$

since the other terms will be small or zero.

A synchronous detection allows us to obtain the term $R_{pp}(1w)$ directly. If a Fourier analysis is made directly on the detected signal (e.g. with the acquisition card software), $R_{pp}(0)$, $R_{pp}(1w)$, $R_{pp}(2w)$ . . . can be obtained separately and, then, these parameters can be divided to obtain $\delta_{pp}$. A simple way to produce a periodic magnetization in the transversal case is by making it rotate in the sample plane with rotating magnets (it can be made oscillate with non-rotating coils). Thus, the rotation frequency of the magnets (equal to the rotation frequency of the magnetization) is introduced as a reference in a synchronous detector, which will give the term $R_{pp}(1w)$ directly as an output.

In the case of measurement in polar or longitudinal configuration, it can also be an advantage to measure with a magnetization that changes periodically, in order to perform the synchronous detection or Fourier analysis. The synchronous detection (lock-in) is very often used to detect signals, since it allows detections to be performed with less noise and greater sensitivity.

The device can consist of electronic data processing means configured to process detector output signals corresponding to at least one such feature of the reflected light. An optimization of signal treatment and analysis can be achieved by means of appropriate software. Logically, such electronic processing means can be associated to the control system, to operate in coordination with the magnetization means and with possible changes in the direction of incidence (angle of incidence θ) or light wavelength on the metallic layer.

For example, the electronic data processing means can be synchronized with the magnetization means, so that changes in at least one such feature of the reflected light are analysed synchronously with changes in the metallic layer magnetization state (something important if what one wishes to detect are the relative differences in reflectivity, $\delta_{pp}$, of the light in transversal magnetization configuration).

The detector can be configured to detect the intensity ($R_{pp}$) of the reflected light and the electronic data processing means can be configured to determine the difference in the intensity of the reflected light ($\Delta R_{pp}$) between two specific magnetization states of the ferromagnetic layer(s). In such case, the electronic data processing means can be configured to calculate the ratio $\delta_{pp}$ between such difference ($\Delta R_{pp}$) in intensity of the reflected light and the chosen reference intensity of the reflected light ($R_{ppREF}=R_{pp}(M_{ref})$).

The device can be configured to detect changes in the refractive index ($n_d$) of the dielectric medium from at least one feature of such detected light as a function of the angle of incidence (θ) of the light on the metallic layer. This configuration can be similar to that of the aforementioned conventional systems, with the difference that not only the intensity of the reflected light is measured, but also the magneto-optic effects, e.g. the light rotation and/or ellipticity or, in the case of transversal configuration, the relative differences in intensity between 2 given transversal magnetization states.

The device can be configured to detect changes in the refractive index ($n_d$) of the dielectric medium from at least one feature of such detected light as a function of the wavelength of the light reflected by the metallic layer.

The device can comprise a plurality of superimposed metallic layers, at least one of those layers containing ferromagnetic material.

In practice, it may be advisable to have several layers, e.g. one layer with ferromagnetic material whereto a layer of a corrosion-resistant metal (e.g. gold) has been applied, and which is the one in contact with the dielectric medium (in practical applications, very often corrosive).

The magneto-optic effects critically depend on the thickness of the metallic layers and on the light wavelength. The optimal thickness(es) and the magneto-optic effects can be accurately estimated in the aforementioned form. In order to excite the surface plasmon wave in the case of ferromagnetic metallic layers, the same techniques as the ones used for conventional sensors described above can be used (prism coupling, periodic structure or guided light).

Another aspect of the invention relates to a method for detecting changes in the refractive index of a dielectric medium, which comprises the following steps:

directing transversal magnetic polarized light (also known as "TM polarization" or "p polarization", i.e. with the electric field inside the plane of light incidence) at a metallic layer (300) by means of the selector coupling means, so that the light can excite surface plasmon resonance on the metallic layer when falling on the metallic layer, and so that at least one part of the light is reflected by the metallic layer, towards a detector (31);

detecting, with the detector, at least one feature of such reflected light and producing at least one detection signal corresponding to at least one such feature;

analysing such detection signal and determining, from such signal, at least one aspect related to the refractive index of the dielectric medium;

characterized in that a metallic layer (300) with ferromagnetic material is used.

For example, the metallic layer can:

be made of ferromagnetic material (only one ferromagnetic material or a combination of several ferromagnetic materials);

be an alloy of at least one ferromagnetic material and at least one non-ferromagnetic material;

be formed by magnetic particles embedded in a metallic medium (e.g. cobalt particles in gold); or be formed by a set of metallic particles that have ferromagnetic material embedded in a dielectric medium.

What has been stated above regarding the device of the invention is also applicable to the method, mutatis mutandis.

The method can comprise the step of magnetizing the metallic layer, for example, in polar configuration (in which case changes in rotation and/or ellipticity of the reflected light can be analysed, for example), in longitudinal configuration (in which case changes in rotation and/or ellipticity of the reflected light can be analysed, for example), or in transversal configuration (in which case relative differences $\delta_{pp}$ in the intensity of the reflected light can be analysed, when varying the magnetization state between 2 given states of transversal magnetization). The magnetization state (i.e. direction and/or module) of the metallic layer can be varied sequentially, as described above.

The aspect related to the refractive index of the dielectric medium that is determined can be:

an absolute value of the refractive index; and/or an indication of whether a change in the refractive index has been produced; and/or an indication of a magnitude of a change in the refractive index.

In the case of sequential variation of the magnetization state of the metallic layer, the step of analysing the detection signal can be performed simultaneously with the variation of the magnetization state, so that changes in such signal are analysed simultaneously with changes in the magnetization state of the metallic layer. In this case, the detection signal can be an indicative signal of (e.g. proportional to) the intensity ($R_{pp}$) of the reflected light, then, the step of analysing the detection signal can comprise the following steps: determining the difference ($\Delta R_{pp}$) in the intensity of the reflected light between 2 given magnetization states, divided by an intensity of reference $R_{ppREF}$; and relating the operation result to the refractive index of the dielectric medium.

Instead of a single metallic layer, a set of metallic layers can be used, at least one of them having ferromagnetic material.

BRIEF DESCRIPTION OF THE DRAWINGS

In order to help towards a better understanding of this invention, a series of drawings are very briefly described below, some of which are specifically related to an embodiment of such invention, being an illustrative and non-restrictive example thereof.

FIG. 11A is a diagram showing the variations in the intensity of the reflected light in a simulation of a practical case wherein the measurement has been taken in accordance with the state of the art, while

DESCRIPTION OF A PREFERRED EMBODIMENT OF THE INVENTION

Figure 10:
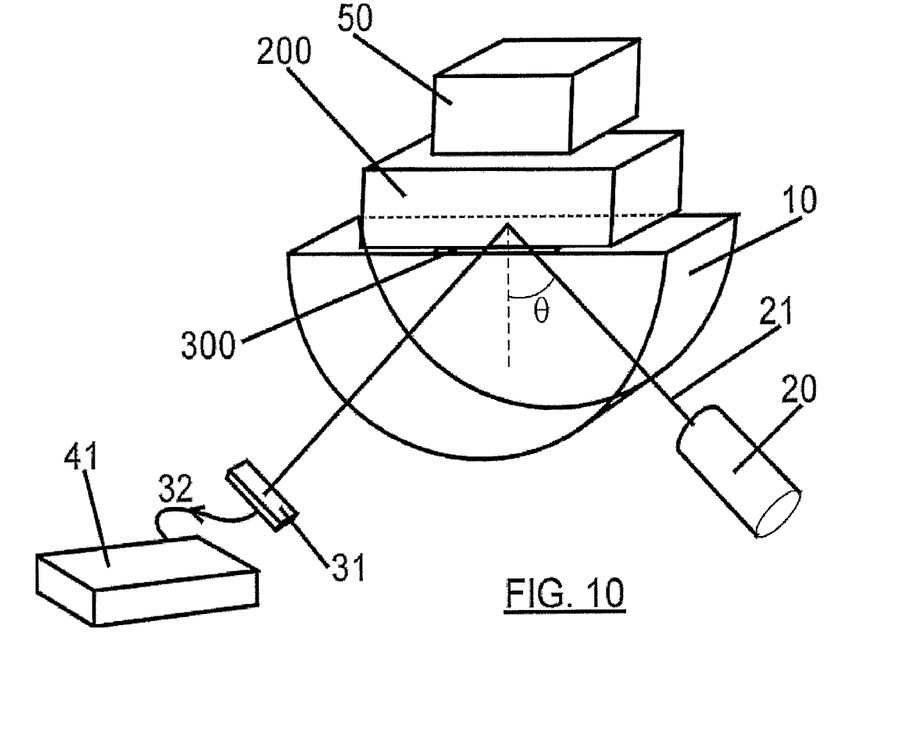
FIG. 10 shows a configuration in accordance with a preferred embodiment of the invention.

FIG. 10 shows a device configuration in accordance with a preferred embodiment of the invention, which comprises:

a metallic layer 300 with ferromagnetic material (e.g. iron, cobalt or nickel), placed on a surface of a prism 10 (e.g. in direct contact or through a medium having the same refractive index as the prism) and with its free surface in contact with a dielectric medium 200 (the prism is used for the required coupling in order to produce the plasmon resonance);

a light source 20 which directs TM polarized light 21 towards such metallic layer 300, so that the light is reflected by such metallic layer; and a detector 31 (e.g. a photodiode) configured to receive light reflected by the metallic layer and to detect at least one feature of such reflected light (e.g. its rotation, ellipticity and/or intensity). The detector produces an output signal 32 which indicates the feature(s) detected and which is analysed in an electronic data processing device 41, which can be part of a computer or similar.

The magnetizing element 50 can magnetize the metallic layer 300 in different ways, as a function of the control signals applied to such magnetizing element. For example, as a function of such signals, the magnetizing element can magnetize the metallic layer in polar configuration (similar to that shown in FIG. 7A), longitudinal configuration (similar to that shown in FIG. 7B), and/or transversal configuration (similar to that shown in FIG. 7C). The selection of the magnetization type will depend on the light features one wishes to detect and taken as a base for the subsequent determination of the dielectric medium refractive index.

Figure 11A:
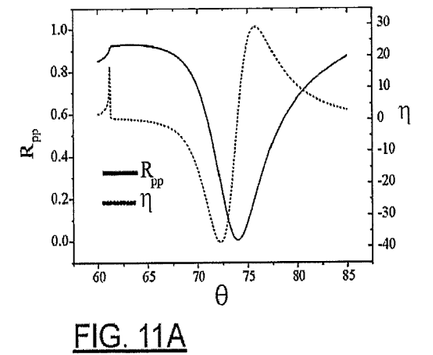
Figure 11B:
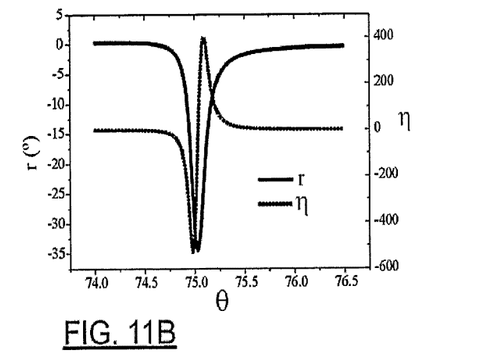
FIGS. 11B-11D are diagrams showing measurements of light features in system simulations in accordance with preferred embodiments of the invention.

For example, magnetization in polar or longitudinal configuration can be appropriate if the light feature one wishes to measure is its rotation (r) and/or ellipticity (e). FIGS. 11B and 11D show respectively measurements of "r" rotation and "e" ellipticity, as a function of the angle of light incidence θ, in a simulation with polar magnetization, as well as the estimated sensitivity η of the sensor with this configuration (the sensitivity has been calculated with the following formula $$\eta = (1/S_{max}) \times (\partial S/\partial n_d),$$

where $S_{max}$ is the maximum value of the measured signal, S is the value of the measured signal, and $n_d$ is the refractive index of the dielectric medium). That is, the sensitivity η of the sensor with regard to changes in the refractive index is defined as the variation of the measured signal as a function of the variation of the refractive index of the dielectric, standardized to the maximum value of the signal. As observed by comparing the sensitivity η in the diagrams of FIGS. 11B and 11D to the sensitivity in the diagram of FIG. 11A, which shows the intensity $R_{pp}$ of the reflected light in a configuration in accordance with the state of the art (with 50 nm-thick gold layer), at least in theory, the invention allows much greater sensitivity to be obtained (increased with a factor greater than 10).

On the other hand, magnetization in transversal configuration may be preferable if the intensity of the reflected light is to be measured, and the analysis is to be based on the relative differences, $\delta_{pp}$, in such intensity according to the magnetization state. In this case, the magnetizing element 50 can be configured so that it generates a sequential magnetic field, e.g. changing the magnetization direction within the transversal configuration or rotating the magnetization within the layer plane, i.e. a sequential change in the magnetization state of the metallic layer is established. Then, measurements of light intensity $R_{pp}$ can be taken at two specific moments of transversal magnetization, and the differences of relative intensity $\delta_{pp}$ between those magnetization states can be taken as a base to determine (changes in) the reflectivity indexes. This can be done by synchronizing the analysis of the output signals of the detector 41 with the magnetization element 50 controller and by making a synchronous detection.

Figure 11C:
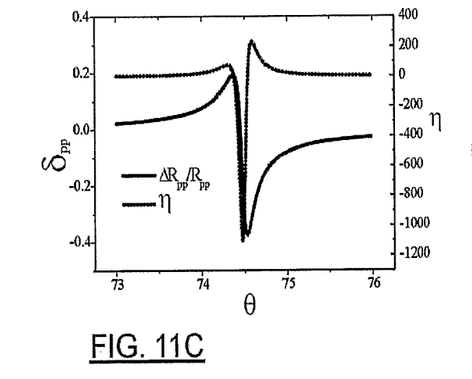
Figure 11D:
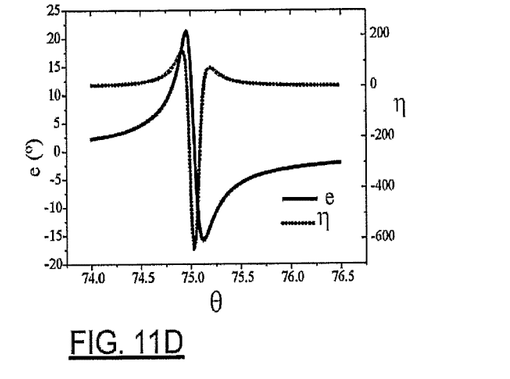

FIG. 11C shows the results of a simulation of a $\delta_{pp}$ detection as a function of the angle of incidence θ and with transversal magnetization with alternating direction, as well as the estimate of the corresponding sensitivity η. Also, in this case, the results of the simulation suggest a sensitivity increase with a factor greater than 10 with regard to the conventional case of FIG. 11A.

Figure 12:
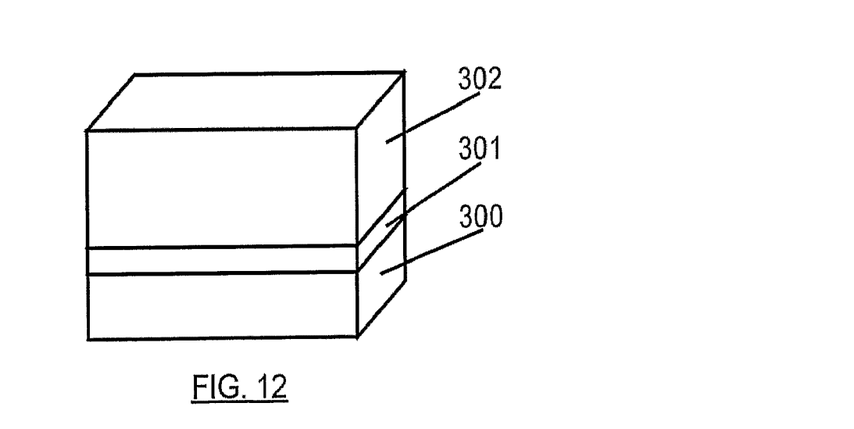
FIG. 12 shows a set of metallic layers suitable for a practical embodiment of the invention.

FIG. 12 briefly shows a set of layers which comprises:

a first 14 nm-thick cobalt layer 300 located on the prism 10 (e.g. in direct contact or through a medium having the same refractive index as the prism);

a second 1 nm-thick chromium layer 301 which is used to provide the deposit/adherence of a third layer on the first layer;

the third 29 nm-thick gold layer 302 in contact with the dielectric medium.

Given that gold is very resistant to corrosion, the first layer 300 is protected from the corrosive effects which some dielectric media may have.

With the described configuration, there are multiple ways for detecting changes in the dielectric medium which affect its refractive index. Basically, light has two variables, namely, the angle of incidence θ and the wavelength λ. Therefore:

i. The wavelength can be kept fixed and the angle of incidence can be varied (obtaining curve types like those shown in FIGS. 11B-11D)

ii. The angle of incidence can be kept fixed and the wavelength can be varied.

iii. Both the wavelength and the angle of incidence can be varied.

iv. Both the wavelength and the angle of incidence can be kept constant, and changes in the features of the detected signal can be measured ($\delta_{pp}$ in case of transversal magnetization, and rotation and/or ellipticity in case of magnetization in polar or longitudinal configuration).

The disclosed device can be used, for example, as refractometer, chemical sensor, or biosensor.

The materials, dimensions, shape and arrangement of the elements are subject to variation, provided that this does not involve an alteration of the basic concept of the invention.

Throughout the present description and claims, the term "comprises" and variations thereof, such as "comprising", do not intend to exclude other steps or components.

The invention claimed is:

1. A device for detecting changes in the refractive index of a dielectric medium (200), this device comprising:
    at least one metallic layer (300) configured to be placed in contact with the dielectric medium (200);
    at least one light source (20) configured to direct transversal magnetic polarized light towards said metallic layer, so that the light falls on said metallic layer;
    coupling means (10) associated to said light source (20) and to said metallic layer (300), so that the light can excite surface plasmon resonance on the metallic layer when falling on the metallic layer;
    at least one detector (31) configured to receive light reflected by the metallic layer and to detect at least one feature of said light;
    wherein
    the metallic layer contains ferromagnetic material;
    characterized in that
    the device further comprises magnetization means (50) configured to magnetize the metallic layer (300).

2. A device, according to claim 1, characterized in that the magnetization means (50) are configured to magnetize the metallic layer in polar configuration.

3. A device, according to claim 2, characterized in that the magnetization means (50) are configured to be able to sequentially vary the magnetization state of the metallic layer (300).

4. A device, according to claim 3, characterized in that the electronic data processing means (41) are synchronized with the magnetization means, so that changes in at least one such feature of the reflected light are analysed synchronously with changes in the magnetization state of the metallic layer (300).

5. A device, according to claim 2, characterized in that the detector is configured to detect, at least, changes in the rotation (r) and/or ellipticity (e) of the reflected light.

6. A device, according to claim 1, characterized in that the magnetization means (50) are configured to magnetize the metallic layer in longitudinal configuration.

7. A device, according to claim 6, characterized in that the detector is configured to at least detect changes in the rotation (r) and/or ellipticity (e) of the reflected light.

8. A device, according to claim 1, characterized in that the magnetization means (50) are configured to magnetize the metallic layer in transversal configuration.

9. A device, according to claim 8, characterized in that the detector is configured to detect the intensity ($R_{pp}$) of the reflected light and by that the electronic data processing means are configured to determine the difference ($\Delta R_{pp}$) in the reflected light intensity between 2 given transversal magnetization states.

10. A device, according to claim 9, characterized in that the electronic data processing means are configured to calculate the ratio ($\delta R_{pp}$) between such difference ($\Delta R_{pp}$) in the intensity of the reflected light and a reference intensity ($R_{ppREF}$) of the reflected light.

11. A device, according to claim 1, characterized in that it also comprises electronic data processing means (41) configured to process output signals (32) from the detector (31) corresponding to at least one such feature of the reflected light.

12. A device according to claim 1, characterized in that it is configured to detect changes in the refractive index ($n_d$) of the dielectric medium from at least one feature of such detected light, as a function of the angle of incidence ($\theta$) of the light on the metallic layer (300).

13. A device according to claim 1, characterized in that it is configured to detect changes in the refractive index ($n_d$) of the dielectric medium from at least one feature of such detected light, as a function of the wavelength of the reflected light over the metallic layer (300).

14. A device according to claim 1, characterized in that the metallic layer is of ferromagnetic material.

15. A device according to claim 1, characterized in that the metallic layer is an alloy between at least one ferromagnetic material and at least one non-ferromagnetic material.

16. A device according to claim 1, characterized in that the metallic layer is formed by magnetic particles embedded in a metallic medium.

17. A device according to claim 1, characterized in that the metallic layer is formed by a set of metallic particles with ferromagnetic material embedded in a dielectric medium.

18. A device according to claim 1, characterized in that it comprises a plurality of superimposed metallic layers, at least one of said layers (300) having ferromagnetic material.

19. A device according to claim 18, wherein said plurality of superimposed metallic layers comprises, in addition to said layer (300) having ferromagnetic material, a layer (302) of a corrosion-resistant metal.

20. A device according to claim 19, wherein said corrosion-resistant metal is gold.

21. A device according to claim 19, wherein the layer (302) of a corrosion-resistant material and the layer (300) having ferromagnetic material are separated by a further layer (301) used to provide adherence between the layer (302) of a corrosion-resistant material and the layer (300) having ferromagnetic material.

22. A device according to claim 21, wherein said further layer (301) is a chromium layer.

23. A device according to claim 18, wherein said plurality of superimposed metallic layers comprises a cobalt layer making up said layer (300) having ferromagnetic material, said plurality of superimposed layers further comprising a gold layer (302), said gold layer (302) being separated from said cobalt layer (300) by a chromium layer (301).

24. A device according to claim 18, wherein said plurality of superimposed metallic layers comprises a further layer for providing adherence to the layer having ferromagnetic material.

25. A device according to claim 24, said layer for providing adherence being a chromium layer.

26. A device according to claim 1, wherein said at least one metallic layer has a thickness selected so as to optimise surface plasmon resonance.

27. A method for detecting changes in the refractive index of a dielectric medium, which comprises the following steps:
    directing transversal magnetic polarized light towards a metallic layer (300) through coupling means selected in a way that the light can excite surface plasmon resonance on the metallic layer when falling on the metallic layer and in a way that at least one part of the light is reflected by the metallic layer, towards a detector (31);

detecting, with the detector, at least one feature of such reflected light and producing at least one detection signal (32) corresponding to at least one such feature; analysing such detection signal and determining, from such signal, at least one aspect related to the refractive index of the dielectric medium.
wherein
a layer containing a ferromagnetic material is used for the metallic layer (300);
characterized in that
the method further comprises the step of magnetizing the metallic layer (300).

28. A method, according to claim 27, characterized in that the metallic layer is magnetized in polar configuration.

29. A method, according to claim 28, characterized in that the magnetization state of the metallic layer (300) is varied sequentially.

30. A method, according to claim 29, characterized in that the step of analysing the detection signal is performed synchronously with the variation of the magnetization state, so that changes in such signal are analysed synchronously with the variation of the magnetization state of the metallic layer (300).

31. A method according to claim 28, characterized in that at least changes in rotation (r) and/or ellipticity (e) of the reflected light are analysed.

32. A method, according to claim 27, characterized in that the metallic layer is magnetized in longitudinal configuration.

33. A method, according to claim 27, characterized in that the metallic layer is magnetized in transversal configuration.

34. A method, according to claim 33, characterized in that the detection signal indicates the intensity ($R_{pp}$) of the reflected light and characterized in that the step of analysing the detection signal comprises determining the difference ($\Delta R_{pp}$) in the intensity of the reflected light between two different transversal magnetization states, and relating such difference to the refractive index of the dielectric medium.

35. A method, according to claim 34, characterized in that the step of analysing the detection signal comprises calculating a ratio ($\delta_{pp}$) between such difference ($\Delta R_{pp}$) in the intensity of the reflected light and a reference intensity $R_{ppREF}$ of the reflected light.

36. A method, according to claim 27 characterized in that at least one such aspect related to the refractive index of the dielectric medium comprises:
an absolute value of the refractive index; and/or
an indication of whether a change in the refractive index has been produced; and/or
an indication of a magnitude of a change in the refractive index.

37. A method according to claim 27, characterized in that the metallic layer (300) containing ferromagnetic material is part of a plurality of superimposed metallic layers.

38. A method according to claim 37, wherein said plurality of superimposed metallic layers comprises, in addition to said layer (300) having ferromagnetic material, a layer (302) of a corrosion-resistant metal.

39. A method according to claim 38, wherein said corrosion-resistant metal is gold.

40. A method according to claim 38, wherein the layer (302) of a corrosion-resistant material and the layer (300) having ferromagnetic material are separated by a further layer (301) used to provide adherence between the layer (302) of a corrosion-resistant material and the layer (300) having ferromagnetic material.

41. A method according to claim 40, wherein said further layer (301) is a chromium layer.

42. A method according to claim 37, wherein said plurality of superimposed metallic layers comprises a cobalt layer making up said layer (300) having ferromagnetic material, said plurality of superimposed layers further comprising a gold layer (302), said gold layer (302) being separated from said cobalt layer (300) by a chromium layer (301).

43. A method according to claim 37, wherein said plurality of superimposed metallic layers comprises a further layer for providing adherence to the layer having ferromagnetic material.

44. A method according to claim 43, said layer for providing adherence being a chromium layer.

45. A method according to claim 27, wherein said at least one metallic layer has a thickness selected so as to optimise surface plasmon resonance.

* * * * *